United States Patent
Li et al.

(10) Patent No.: US 12,109,436 B2
(45) Date of Patent: Oct. 8, 2024

(54) CONTROL METHOD AND DEVICE FOR POSITIONING, RADIOTHERAPY SYSTEM, AND STORAGE MEDIUM

(71) Applicant: OUR UNITED CORPORATION, Xi'an (CN)

(72) Inventors: Jinsheng Li, Xi'an (CN); Hao Yan, Xi'an (CN); Tianchang Gou, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 241 days.

(21) Appl. No.: 17/883,473

(22) Filed: Aug. 8, 2022

(65) Prior Publication Data
US 2023/0041251 A1 Feb. 9, 2023

(30) Foreign Application Priority Data
Aug. 9, 2021 (CN) .......................... 202110906237.6

(51) Int. Cl.
*A61N 5/10* (2006.01)

(52) U.S. Cl.
CPC .... *A61N 5/1069* (2013.01); *A61N 2005/1059* (2013.01); *A61N 2005/1076* (2013.01)

(58) Field of Classification Search
CPC .......... A61N 5/1069; A61N 2005/1059; A61N 2005/1076
See application file for complete search history.

(56) References Cited

U.S. PATENT DOCUMENTS

| | | | |
|---|---|---|---|
| 2016/0114192 A1* | 4/2016 | Lachaine | A61B 6/032 600/1 |
| 2018/0140222 A1* | 5/2018 | Weber | A61B 5/06 |
| 2018/0325472 A1* | 11/2018 | Lin | A61B 6/08 |

* cited by examiner

*Primary Examiner* — Kiho Kim
(74) *Attorney, Agent, or Firm* — Knobbe Martens Olson & Bear LLP

(57) ABSTRACT

A control method for positioning is provided, which is applicable to a radiotherapy system. The method includes: acquiring a plurality of first body surface coordinates of a target site in a three-dimensional body surface image of a treatment object on a treatment couch; acquiring a plurality of second body surface coordinates under an isocentric coordinate system by transforming the first body surface coordinates using a target transformation matrix corresponding to the first placement position; determining, based on the plurality of second body surface coordinates and a contour image of the target site in the treatment plan, a placement offset of the target site, so as to control the treatment couch to move until the placement offset of the target site upon the movement meets a target offset requirement.

20 Claims, 3 Drawing Sheets

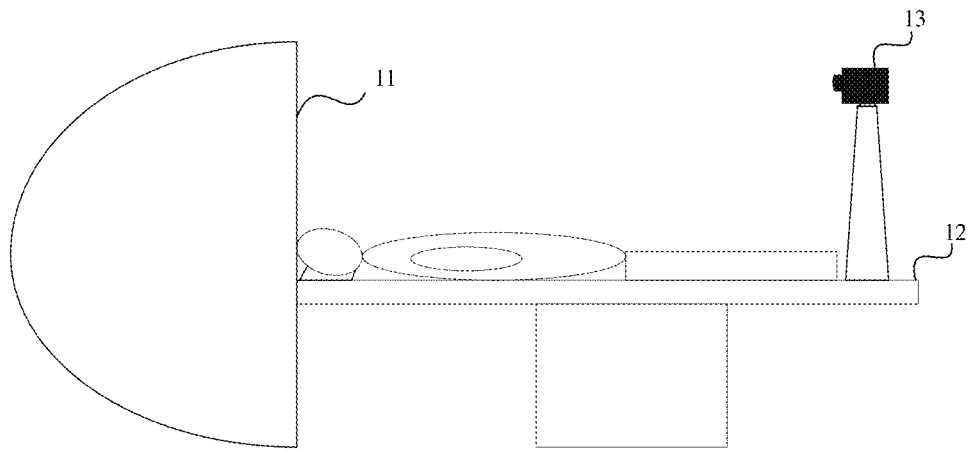

FIG. 1

```
Acquiring a plurality of first body surface coordinates of a target site in a three-dimensional       ~S201
          body surface image of a treatment object on the treatment couch Acquiring a plurality of second body surface coordinates of the target site by transforming
   the plurality of first body surface coordinates using a target transformation matrix             ~S202
               corresponding to the first placement position Determining, based on the plurality of second body surface coordinates and a contour image
of the target site in a treatment plan, a placement offset of the target site under the isocentric   ~S203
coordinate system, so as to control the treatment couch to move until the placement offset of
        the target site upon the movement meets a target offset requirement
```

FIG. 2

CONTROL METHOD AND DEVICE FOR POSITIONING, RADIOTHERAPY SYSTEM, AND STORAGE MEDIUM

CROSS-REFERENCE TO RELATED APPLICATION

This application is based on and claims priority to Chinese Patent Application No. 202110906237.6, filed on Aug. 9, 2021, the disclosure of which is incorporated herein by reference in its entirety.

TECHNICAL FIELD

The present disclosure relates to the technical field of medical equipment, and in particular, to a control method for positioning, a control device therefor, a radiotherapy system, and a storage medium.

BACKGROUND

With the technological development of radiation oncology and material science, oncological radiotherapy, as an important tool for the overall assessment of treatment, should achieve precise locating, accurate planning, and precise positioning.

Positioning in the field of radiotherapy is an important tool to improve the accuracy of radiation therapy and to ensure and control the quality of radiotherapy.

SUMMARY

The present disclosure provides a control method for positioning, a device therefor, a radiotherapy system, and a storage medium.

The technical solutions provided in embodiments of the present disclosure include the following.

In a first aspect, the embodiments of the present disclosure provide a control method for positioning, applicable to a radiotherapy system, the radiotherapy system including radiotherapy equipment and a depth camera, the radiotherapy equipment including a radiation chamber and a treatment couch, and the depth camera being disposed at an end, distal from the radiation chamber, of the treatment couch, the method including:

acquiring a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;

acquiring a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and determining, based on the plurality of second body surface coordinates and a contour image of the target site in a treatment plan, a placement offset of the target site under the isocentric coordinate system, so as to control the treatment couch to move until the placement offset of the target site upon the movement meets a target offset requirement.

Optionally, prior to acquiring the plurality of second body surface coordinates of the target site by transforming the plurality of first body surface coordinates using the target transformation matrix corresponding to the first placement position, the method further including:

acquiring the target transformation matrix by transforming, based on the first placement position and a second placement position of the treatment couch, a transformation matrix corresponding to the second placement position, wherein the second placement position is a placement position different from the first placement position.

Optionally, the treatment couch is a three-dimensional treatment couch; and acquiring the target transformation matrix by transforming, based on the first placement position and the second placement position of the treatment couch, the transformation matrix corresponding to the second placement position includes:

calculating a first amount of translation from the second placement position to the first placement position; and acquiring the target transformation matrix by transforming, based on the first amount of translation, the transformation matrix corresponding to the second placement position.

Optionally, the treatment couch is a six-dimensional treatment couch; and acquiring the target transformation matrix by transforming, based on the first placement position and the second placement position of the treatment couch, the transformation matrix corresponding to the second placement position includes:

calculating an amount of rotation and a second amount of translation from the second placement position to the first placement position; and acquiring the target transformation matrix by transforming, based on the amount of rotation and the second amount of translation, the transformation matrix corresponding to the second placement position.

Optionally, the second placement position is a calibrated placement position of the treatment couch; and prior to acquiring the target transformation matrix by transforming, based on the first placement position and the second placement position of the treatment couch, the transformation matrix corresponding to the second placement position, the method further includes:

acquiring first coordinates of a target position in a depth image of a calibration phantom on the treatment couch, wherein the depth image is captured by the depth camera in response to the treatment couch being at the calibrated placement position, the first coordinates are coordinates under the camera coordinate system, and the target position is any position on the calibration phantom;

determining, based on the first coordinates and a transformation relationship between the camera coordinate system and the treatment couch coordinate system, second coordinates of the target position under the treatment couch coordinate system;

determining, based on the second coordinates and a transformation relationship between the treatment couch coordinate system and the isocentric coordinate system, third coordinates of the target position under the isocentric coordinate system; and calculating, based on the first coordinates and the third coordinates, a transformation matrix corresponding to the calibrated placement position.

Optionally, determining, based on the plurality of second body surface coordinates and the contour image of the target site in the treatment plan, the placement offset of the target site under the isocentric coordinate system includes:

determining, based on the plurality of second body surface coordinates, a first contour of the target site; and determining, based on the contour image and the first contour, the placement offset.

Optionally, the method further includes:

controlling the depth camera to acquire body surface information of the treatment object, so as to monitor the treatment object during treatment.

In a second aspect, the embodiments of the present disclosure provide a control device for positioning. The device is applicable to a radiotherapy system, wherein the radiotherapy system includes radiotherapy equipment and a depth camera, the radiotherapy equipment including a radiation chamber and a treatment couch, and the depth camera being disposed at an end, distal from the radiation chamber, of the treatment couch.

The device includes a processor, and a memory configured to store a computer program executable by the processor; wherein the processor, when loading and running the computer program, is caused to:

acquire a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;

acquire a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and determine, based on the plurality of second body surface coordinates and a contour image of the target site in a treatment plan, a placement offset of the target site under the isocentric coordinate system, so as to control the treatment couch to move until the placement offset of the target site upon the movement meets a target offset requirement.

In a third aspect, the embodiments of the present disclosure further provide a radiotherapy system. The radiotherapy system includes radiotherapy equipment, a depth camera, and one or more processors, the radiotherapy equipment including: a radiation chamber and a treatment couch;

wherein the depth camera is disposed at an end, distal from the radiation chamber, of the treatment couch; and the one or more processors are connected to the depth camera and configured to perform a control method for positioning, wherein the control method for positioning includes:

acquiring a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;

acquiring a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and determining, based on the plurality of second body surface coordinates and a contour image of the target site in a treatment plan, a placement offset of the target site under the isocentric coordinate system, so as to control the treatment couch to move until the placement offset of the target site upon the movement meets a target offset requirement.

In a fourth aspect, the embodiments of the present disclosure further provide a non-transitory computer-readable storage medium. The storage medium stores a computer program, wherein the computer program, when loaded and run by a processor of a device, causes the device to perform the control method for positioning as defined in the first aspect.

BRIEF DESCRIPTION OF THE DRAWINGS

To describe the technical solutions provided in the embodiments of the present disclosure more clearly, the following briefly introduces the accompanying drawings required in the embodiments. It should be noted that the accompanying drawings in the following description show merely some embodiments of the present disclosure and therefore should not be considered as a limitation to the scope, and a person of ordinary skill in the art may still derive other drawings from these accompanying drawings without creative efforts.

FIG. 1 is a schematic diagram of a radiotherapy system according to an embodiment of the present disclosure;

FIG. 2 is a flowchart of a control method for positioning according to an embodiment of the present disclosure;

DETAILED DESCRIPTION

Figure 3:
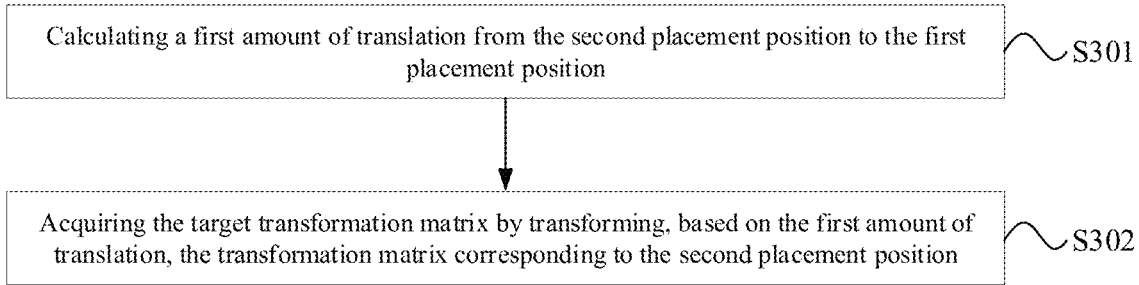
FIG. 3 is a flowchart of a method for acquiring a transformation matrix in a control method for positioning according to an embodiment of the present disclosure.

For clearly illustrating the objects, technical solutions, and advantages of embodiments of the present disclosure, the technical solutions in the embodiments of the present disclosure are completely and clearly described hereinafter with reference to the accompanying drawings of embodiments of the disclosure. It is obvious that the described embodiments are merely part of, but not all embodiments of, the present disclosure.

Positioning techniques in the field of radiotherapy mainly include an image guided radiotherapy (IGRT) technique and a surface guided radiotherapy (SGRT) technique. The SGRT technique is a high-precision treatment positioning guiding technique in which the optical surface camera is mounted at a ceiling or other fixed positions that have a predetermined positional relationship with an isocenter of radiotherapy equipment. During the radiotherapy treatment for a treatment object based on the radiotherapy equipment, it is necessary to control the positioning of the treatment couch based on a three-dimensional body surface image of the treatment object captured by the depth camera, and then monitor the treatment object upon completing the positioning. However, in the current SGRT technique, the depth camera is disposed at a fixed position on the ceiling, therefore the relative position of the camera to the radiotherapy equipment remains constant upon the camera being mounted.

For roller-type radiotherapy equipment, in the case that the camera is mounted at a fixed position that has a fixed relative position relationship with the treatment device, such as the ceiling, the depth camera cannot be used for subsequent treatment monitor upon completing the positioning. For performing the treatment monitor, an additional camera is needed. However, the position calibration of the additional camera with the camera for positioning is complicated, which makes the system design of the whole radiotherapy equipment more difficult and increases the cost of the radiotherapy equipment.

Therefore, how to achieve control for positioning and subsequent monitoring for the treatment object without adding an additional camera is a problem that needs to be solved currently.

For achieving the control for positioning of the radiotherapy equipment and the subsequent monitoring for the treatment object, the embodiments of the present disclosure provide a radiotherapy system. FIG. 1 is a schematic diagram of a radiotherapy system according to an embodiment of the present disclosure. As shown in FIG. 1, the radiotherapy system may include radiotherapy equipment and a depth camera 13. The radiotherapy equipment includes a radiation chamber 11 and a treatment couch 12, wherein a plurality of radiation sources may be provided in the radiation chamber 11. The depth camera 13 may be fixedly disposed at an end, distal from the radiation chamber 11, of the treatment couch 12 and may move with a movement of the treatment couch 12. For example, the depth camera 13 is fixed at an end of a movable bed plate of the treatment couch 12. Illustratively, the depth camera 13 may be fixed at the end, distal from radiation chamber 11, of the treatment couch 12 via a mounting bracket, and a lens of the depth camera 13 may be oriented towards the radiation chamber 11. The mounting bracket may be a bracket with a predetermined height, so as to ensure that the depth camera 13 has a sufficient camera view upon the depth camera 13 being fixedly mounted. The depth camera 13 may be configured to capture a three-dimensional image of a target object such as a calibration phantom or a treatment object on the treatment couch 12. The depth camera 13 may also be referred to as a three-dimensional (3D) camera, or other similar description.

The depth camera 13 fixed on the treatment couch 12 may move with the movement of the treatment couch 12. Therefore, upon controlling the positioning and completing the positioning using the solution of the present disclosure, the depth camera can be seamlessly integrated into the treatment monitor even if a position of a positioning isocenter (i.e., virtual isocenter) is different from a position of a treatment isocenter (i.e., isocenter of the radiotherapy equipment). That is, the body surface information acquired by the depth camera 13 may be sequentially used for the treatment monitor.

It should be explained that for radiotherapy equipment, there are usually two isocenters: a virtual isocenter and an isocenter of the radiotherapy equipment, wherein the isocenter of the radiotherapy equipment may be a radiation focus in the radiation chamber of the radiotherapy equipment, or an intersection point of a beam axis of radiation beams with a rotating axis of the radiotherapy equipment, and the virtual isocenter refers to a position, outside the radiation chamber of the radiotherapy equipment, that has a predetermined positional relationship with the isocenter of the radiotherapy equipment.

Illustratively, there is a predetermined offset between the positioning isocenter and the treatment isocenter along the length of the treatment couch. Upon completing of the positioning, a target point in a target site of a patient on the treatment couch 12 (e.g., a target point or a predetermined point in a target area) coincides with the positioning isocenter, such that the target point in the target site of the patient may coincide with the treatment isocenter only by moving the treatment couch for a predetermined offset.

It should be noted that the radiation chamber 11 shown in FIG. 1 is an example of a radiation chamber matching with a head radiotherapy equipment, and for radiotherapy equipment for other body parts, a relative position of the radiation chamber to the treatment couch 12 may differ from the relative position shown in FIG. 1, which is not limited in the present disclosure.

The radiotherapy system may further include a control device for positioning (not shown in FIG. 1). In practice, the control device for positioning may include at least one of: a computer device, a lower computer disposed in a control cabinet of the radiotherapy equipment, an upper computer that is disposed outside the control cabinet of the radiotherapy equipment and communicatively connected to the control cabinet and interacts with a user, and any processing device that can perform a software processing operation.

The control device for positioning is communicatively connected to the depth camera 13, and configured to acquire the three-dimensional image captured by the depth camera and then perform a control method for positioning provided in the following embodiments of the present disclosure.

Based on any radiotherapy system described above, the embodiments of the present disclosure provide various implementations to control the positioning of radiotherapy equipment. The control method for positioning provided in the present disclosure is illustrated based on a plurality of examples hereinafter.

FIG. 2 is a flowchart of a control method for positioning according to an embodiment of the present disclosure. The method is applicable to any radiotherapy system as described above. The method may be implemented by a control device for positioning by means of software and/or hardware, wherein the control device is communicatively connected to the depth camera. As shown in FIG. 2, the method may include the following processes.

In S201, a plurality of first body surface coordinates of a target site in a three-dimensional body surface image of a treatment object on the treatment couch are acquired. The three-dimensional body surface image is captured by the depth camera in response to the treatment couch being at a first placement position, wherein the first placement position is any position at which the treatment couch is placeable. The plurality of first body surface coordinates are coordinates of a plurality of body surface positions in a region corresponding to the target site under a camera coordinate system of the depth camera.

Prior to performing radiotherapy on the treatment object, it is necessary to control the treatment couch to move to control the radiotherapy positioning, so as to ensure that upon completing the positioning, the target point in the target site of the treatment object on the treatment couch is aligned with the virtual isocenter of the radiotherapy equipment. There is a predetermined positional relationship between the virtual isocenter and the isocenter of the radiotherapy equipment, therefore upon completing the positioning, the target point may be moved to the isocenter of the radiotherapy equipment in the radiation chamber by controlling the treatment couch to move based on the predetermined positional relationship. For example, the predetermined position relationship may include that the virtual isocenter is acquired by moving the isocenter of the radiotherapy equipment for a first distance along a direction away from the radiation chamber. Correspondingly, upon completing the positioning, the target point may be made to be aligned to the isocenter of the radiotherapy equipment in the radiation chamber by controlling the treatment couch to move for a first distance along a direction close to the radiation chamber.

In the case that the target site is moved until the target site is aligned with the isocenter of the radiotherapy equipment, radiation treatment may be performed on the target point by controlling the radiation source in the radiation chamber to emit a radiation beam. For example, the target object may be a patient to be treated, and the target site may be a body part where the lesion is located, such as a head, a part on a body, or a head and neck.

Because the depth camera is fixed at the end, distal from the radiation chamber, of the treatment couch, the depth camera may capture a three-dimensional body surface image of the treatment object on the treatment couch during the movement of the treatment couch toward the radiation chamber. Upon acquiring the three-dimensional body surface image, a plurality of first body surface coordinates of the target site may be acquired by performing coordinate identification on the target site in the three-dimensional body surface image. The plurality of first body surface coordinates may be contour coordinates of the target site in the three-dimensional body surface image.

In S202, a plurality of second body surface coordinates of the target site are acquired by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment.

The target transformation matrix is a transformation matrix between the camera coordinate system of the depth camera and the isocentric coordinate system of the radiotherapy equipment in response to the treatment couch being at the first placement position.

The above plurality of first body surface coordinates acquired from the three-dimensional body surface image are a plurality of coordinates under the camera coordinate system of the depth camera, and the position coordinates in the treatment plan are coordinates under the isocentric coordinate system of the radiotherapy equipment. Therefore, the target transformation matrix may be used to transform the plurality of first body surface coordinates, so as to acquire the plurality of second body surface coordinates.

For example, the target transformation matrix may be $W_1=[R_1\ T_1]$, wherein $R_1$ represents a first coordinate amount of rotation, and $T_1$ represents a first coordinate amount of translation, and the plurality of second body surface coordinates may be acquired by multiplying the plurality of first body surface coordinates with the target transformation matrix $W_1$.

In S203, a placement offset of the target site under the isocentric coordinate system is determined based on the plurality of second body surface coordinates and a contour image of the target site in a treatment plan, so as to control the treatment couch to move until the placement offset of the target site upon the movement meets a target offset requirement.

In this process, upon acquiring the plurality of second body surface coordinates, the contour of the target site of the treatment object on the treatment couch may be determined based on the plurality of second body surface coordinates, and then the placement offset of the target site under the isocentric coordinate system may be determined by comparing the contour of the target site with the contour image in the treatment plan.

In practice, the positioning usually cannot be completed by moving the treatment couch only once. Therefore, upon controlling the treatment couch to move based on the calculated placement offset, a position at which the treatment couch is upon the movement may be determined as a new first placement position, and the above S201-S203 may be performed again until the placement offset of the target site upon the movement meets the target offset requirement. For example, the target offset requirement may be a predetermined positioning accuracy requirement in clinical treatment, which may be predetermined or acquired in real-time.

Upon being calculated every time, the placement offset may be sent to a movement control device of the treatment couch, such that the movement control device may control the treatment couch to move based on the placement offset.

In the control method for positioning provided by the embodiments of the present disclosure, the plurality of second body surface coordinates of the target site under the isocentric coordinate system may be acquired by transforming the coordinate system of the plurality of first body surface coordinates of the target site using the target transformation matrix corresponding to the first placement positioning, wherein the plurality of first body surface coordinates of the target site are acquired in response to the treatment couch being at the first placement position, and then the placement offset of the target site under the isocentric coordinate system is determined based on the plurality of second body surface coordinates and the contour image of the target site in the treatment plan, such that the treatment couch can be controlled to move until the positioning is completed. In this method, the depth camera fixed at the end, distal from the radiation chamber, of the treatment couch can move with the movement of the treatment couch, that is, the position of the depth camera is changeable. Therefore, upon completing the positioning of the treatment couch based on the three-dimensional body surface images captured by the depth camera, the treatment object can be monitored during treatment based on the images captured by the depth camera without adding an additional camera. In other words, in the present disclosure, both precise control for the positioning of the treatment couch and the monitoring for the treatment object can be achieved without increasing the system design difficulty and system cost of the radiotherapy equipment.

In one possible implementation, the target transformation matrix may be a transformation matrix acquired in advance at the first placement position, such as a transformation matrix acquired during a calibration process based on a phantom. For example, transformation matrixes for a plurality of placement positions may be acquired in advance at the plurality of placement positions using the calibration phantom.

In another possible implementation, it is not necessary to acquire the transformation matrixes corresponding to the plurality of placement positions in advance using the calibration phantom, but only to acquire one transformation matrix corresponding to one placement position and then acquire transformation matrixes corresponding to other positions by transforming the transformation matrix corresponding to the above one position based on the transformation matrix corresponding to the above one position. Accordingly, prior to acquiring the plurality of second body surface coordinates of the target site under the isocentric coordinate system of the radiotherapy equipment by transforming the plurality of first body surface coordinates using the target transformation matrix corresponding to the first placement position in S202, the method further includes: acquiring the target transformation matrix by transforming, based on the first placement position and a second placement position of the treatment couch, a transformation matrix corresponding to the second placement position.

The second placement position is a different placement position from the first placement position, such as a placement position at which the treatment couch is placed prior to the treatment couch being moved to the first placement position (i.e., a previous placement position) or a calibrated placement position of the treatment couch.

The depth camera is fixed at the end, distal from the radiation chamber, of the treatment couch, therefore, the relative position of the depth camera to the isocenter of the radiotherapy equipment may change with the movement of the treatment couch. For the first movement of the treatment couch, the second placement position may be the calibrated placement position, and the target transformation matrix may be acquired by transforming the transformation matrix corresponding to the calibrated placement position based on the placement position upon the first movement (i.e., the first placement position) and the calibrated placement position, so as to update the transformation matrix. For each subsequent movement, the second placement position may be a previous placement position, and for each movement of the treatment couch, the target transformation matrix may be acquired by transforming the transformation matrix corresponding to the previous placement position based on the placement position upon the movement (i.e., the first placement position) and the previous placement position, so as to achieve the update of the transformation matrix.

In the method provided by this embodiment, the target transformation matrix may be acquired by updating the transformation matrix corresponding to the second placement position based on the current placement position (i.e., the first placement position) and the second placement position different from the first placement position, which in turn can avoid the inaccuracy of the transformation matrix caused by the movement of the treatment couch, effectively ensure the accuracy of the transformation matrix between coordinate systems, improve the accuracy of the coordinate transformation, and also effectively ensure the accuracy of the control for positioning.

On the basis of the above control method for positioning, the embodiments of the present disclosure further provide a possible way, for the case that the treatment couch is a three-dimensional treatment couch, to acquire the transformation matrix in the control method for positioning.

FIG. 3 is a flowchart of a method for acquiring a transformation matrix in the control method for positioning according to an embodiment of the present disclosure. As shown in FIG. 3, in the case that the treatment couch is the three-dimensional treatment couch, the above-mentioned acquiring the target transformation matrix by transforming, based on the first placement position and the second placement position of the treatment couch, the transformation matrix corresponding to the second placement position may include the following processes.

In S301, a first amount of translation from the second placement position to the first placement position is calculated.

In the case that the treatment couch is a three-dimensional treatment couch, the movement of the treatment couch only includes translation and does not include rotation.

For example, assuming that the first placement position is $[A_1 \ B_1 \ C_1]$ and the second placement position is $[A_2 \ B_2 \ C_2]$, the first amount of translation may be acquired by calculating the deviation of the position in each of the three coordinate directions based on the first placement position and the second placement position, wherein the first amount of translation can be represented as $[(A_1-A_2) \ (B_1-B_2) \ (C_1-C_2)]$.

In S302, the target transformation matrix is acquired by transforming, based on the first amount of translation, the transformation matrix corresponding to the second placement position.

Assuming that the transformation matrix corresponding to the second placement position is $W_2=[R_2 \ T_2]$, wherein $R_2$ represents a second coordinate amount of rotation, and $T_2$ represents a second coordinate amount of translation, and the target transformation matrix is $W_1=[R_1 \ T_1]$, because the three-dimensional treatment couch can only be translated and cannot be rotated, the $R_1$ can be equal to $R_2$, and $T_1$ can be acquired by calculating based on $T_2$ and the first amount of translation. That is, the target transformation matrix can be acquired as $W_1=[R_1 \ T_1]$.

The method provided in the embodiment provides a simple way for matrix transformation for the three-dimensional treatment couch, based on which the target transformation matrix may be acquired, and the accuracy of subsequent positioning control for the case of the three-dimensional treatment couch can be ensured.

Figure 4:
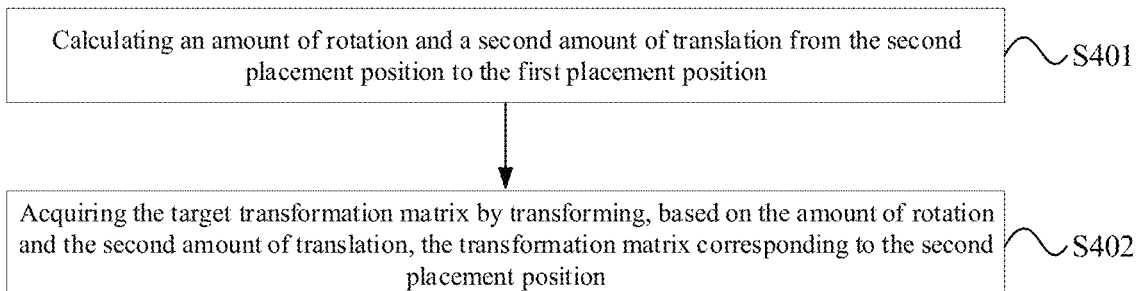
FIG. 4 is a flowchart of another method for acquiring a transformation matrix in a control method for positioning according to an embodiment of the present disclosure.

Based on the above control method for positioning, the embodiments of the present disclosure further provide a possible way to acquire the transformation matrix in the control method for positioning for the case that the treatment couch is a six-dimensional treatment couch. FIG. 4 is a flowchart of another method of acquiring a transformation matrix in a control method for positioning according to an embodiment of the present disclosure. As shown in FIG. 4, in the case that the treatment couch is a six-dimensional treatment couch, the above-mentioned acquiring the target transformation matrix by transforming, based on the first placement position and the second placement position of the treatment couch, the transformation matrix corresponding to the second placement position may include the following processes.

In S401, an amount of rotation and a second amount of translation from the second placement position to the first placement position is calculated.

In the case that the treatment couch is a six-dimensional treatment couch, the movement of the treatment couch includes both translation and rotation.

For example, assuming that the first placement position is $[A_1 \ B_1 \ C_1]$ and the second placement position is $[A_2 \ B_2 \ C_2]$, the second amount of translation may be acquired by calculating, based on the first placement position and the second placement position, the position deviation in the three coordinate directions, that is, the second amount of translation can be represented as $[(A_1-A_2) \ (B_1-B_2) \ (C_1-C_2)]$. In addition, it is necessary to calculate the amount of rotation based on the first placement position and the second placement position.

In S402, the target transformation matrix is acquired by transforming, based on the amount of rotation and the second amount of translation, the transformation matrix corresponding to the second placement position.

Assuming that the transformation matrix corresponding to the second placement position is $W_2=[R_2 \ T_2]$, wherein $R_2$ represents the second coordinate amount of rotation, and $T_2$ represents the second coordinate amount of translation, and the target transformation matrix is $W_1=[R_1 \ T_1]$, because the six-dimensional treatment couch, in addition to being translated, can also be rotated, the difference between the present embodiment and the above embodiment corresponding to the case of the three-dimensional treatment couch is that in the implementation provided in the present embodiment, $R_1$ is not equal to $R_2$, but acquired based on $R_2$ and the amount of rotation acquired by calculating in S401, and $T_1$ is acquired by calculating based on $T_2$ and the second amount of translation acquired by calculating in S401. In this way, the target transformation matrix can be acquired as $W_1=[R_1 \ T_1]$.

The method provided by this embodiment provides an implementation way for matrix transformation for the six-dimensional treatment couch, based on which the target transformation matrix can be acquired and the accuracy of the subsequent positioning control for the six-dimensional treatment couch can be ensured.

The positioning control usually cannot be completed by moving the treatment couch only once. In the case that the first placement position is a placement position at which the treatment couch is placed upon a first movement during the positioning control process, the corresponding second placement position is the calibrated placement position of the treatment couch. The calibrated placement position refers to a placement position of the treatment couch during the calibration process for the transformation matrix, that is, the placement position of the treatment couch in response to a predetermined position on the calibration phantom coinciding with the virtual isocenter of the radiotherapy equipment during the transformation matrix calibration process.

Figure 5:
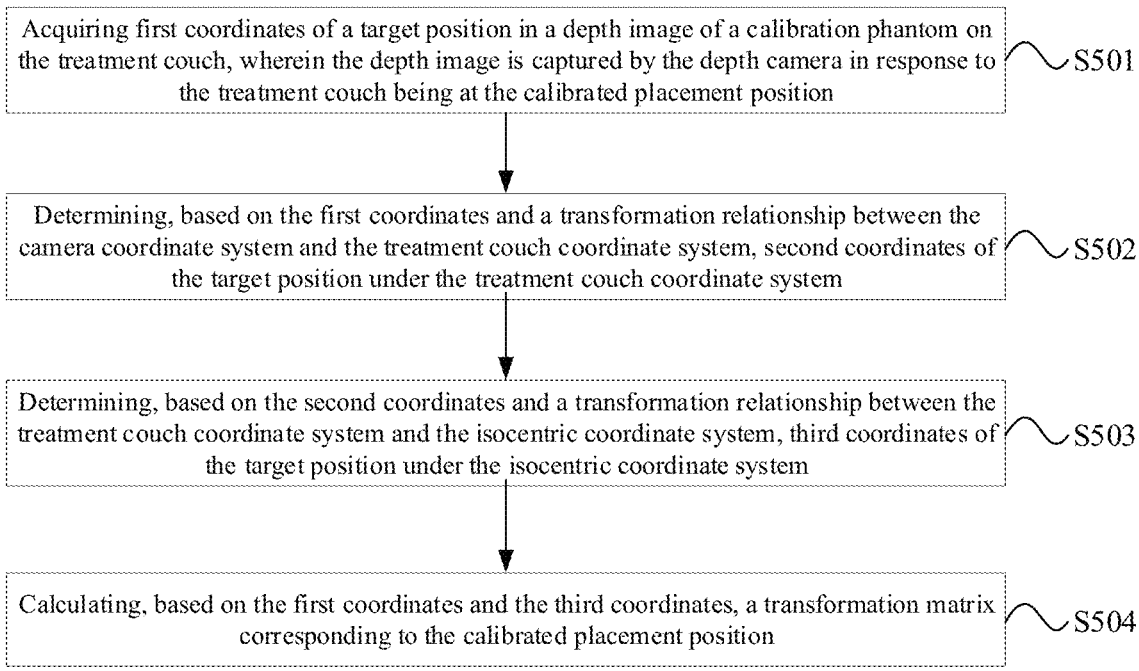
FIG. 5 is a flowchart of yet another method for acquiring a transformation matrix in a control method for positioning according to an embodiment of the present disclosure.

The process of acquiring the transformation matrix corresponding to the calibrated placement position during the calibration process is described hereafter using a specific example. FIG. 5 is a flowchart of another method for acquiring a transformation matrix in a control method for positioning according to an embodiment of the present disclosure. As shown in FIG. 5, prior to acquiring the target transformation matrix by transforming, based on the first placement position and the second placement position of the treatment couch, the transformation matrix corresponding to the second placement position, the method further includes the following processes.

In S501, first coordinates of a target position in a depth image of a calibration phantom on the treatment couch are acquired, wherein the depth image is captured by the depth camera in response to the treatment couch being at the calibrated placement position, the first coordinates are coordinates under the camera coordinate system, and the target position is any position on the calibration phantom.

In S502, second coordinates of the target position under the treatment couch coordinate system are determined based on the first coordinates of the target position and a transformation relationship between the camera coordinate system and the treatment couch coordinate system.

The transformation relationship between the camera coordinate system and the treatment couch coordinate system may be pre-acquired or acquired in real-time. The target position may be any predetermined position on the calibration phantom.

In S503, third coordinates of the target position under the isocentric coordinate system are determined based on the second coordinates and a transformation relationship between the treatment couch coordinate system and the isocentric coordinate system.

The transformation relationship between the treatment couch coordinate system and the isocentric coordinate system may be acquired in advance or in real-time.

In S504, a transformation matrix corresponding to the calibrated placement position is calculated based on the first coordinates and the third coordinates.

During the calibration process, the calibration phantom may be placed on the treatment couch, and the depth camera may be configured to capture the depth image of the calibration phantom. The first coordinates of the target position may be acquired by performing coordinate recognition on the target position in the depth image of the calibration phantom, and the second coordinates may be acquired by transforming the first coordinates of the target position from the camera coordinate system to the treatment couch coordinate system based on a predetermined transformation relationship between the camera coordinate system and the treatment couch coordinate system. Subsequently, the third coordinates may be acquired by transforming the second coordinates from the treatment couch coordinate system to the isocentric coordinate system based on a predetermined transformation relationship between the treatment couch coordinate system and the isocentric coordinate system.

Upon acquiring the third coordinates, it is necessary to compare the third coordinates with the coordinates of the virtual isocenter of the radiotherapy equipment. In the case that the third coordinates are aligned with the coordinates of the virtual isocenter, it may be determined that the predetermined position on the calibration phantom is aligned with the virtual isocenter, and then it may be determined that the treatment couch is moved to the calibrated placement position.

The target position on the calibration phantom may be provided with a predetermined marker, and the coordinates of the target position may be acquired by performing coordinate recognition on the predetermined marker.

In the case that it is determined that the treatment couch is moved to the calibrated placement position, the transformation matrix corresponding to the calibrated placement position may be acquired based on the first coordinates and third coordinates acquired in the case that the treatment couch is at the calibrated placement position.

For example, the calibrated placement position may be $[A_0\ B_0\ C_0]$, the above camera coordinate system may be $[X\ Y\ Z]$, the treatment couch coordinate system may be $[A\ B\ C]$, and the isocentric coordinate system may be $[a\ b\ c]$. In this way, by implementing this embodiment, the camera coordinate system $[X\ Y\ Z]$ and the isocenter coordinate system $[a\ b\ c]$ can be calibrated, and the transformation matrix between the camera coordinate system $[X\ Y\ Z]$ and the isocentric coordinate system $[a\ b\ c]$ can be acquired, i.e., the transformation matrix corresponding to the calibrated placement position $W=[R\ T]$ can be acquired, wherein R represents the coordinate amount of rotation in the case that the treatment couch is at the calibrated placement position, and T represents the coordinate amount of translation in the case that the treatment couch is at the calibrated placement position.

In the method provided by this embodiment, the transformation matrix corresponding to the calibrated placement position may be acquired by calibrating the coordinate systems based on the calibration phantom during the calibration process, which can effectively ensure the accuracy of the subsequent positioning control based on the transformation matrix corresponding to the calibrated placement position.

Figure 6:
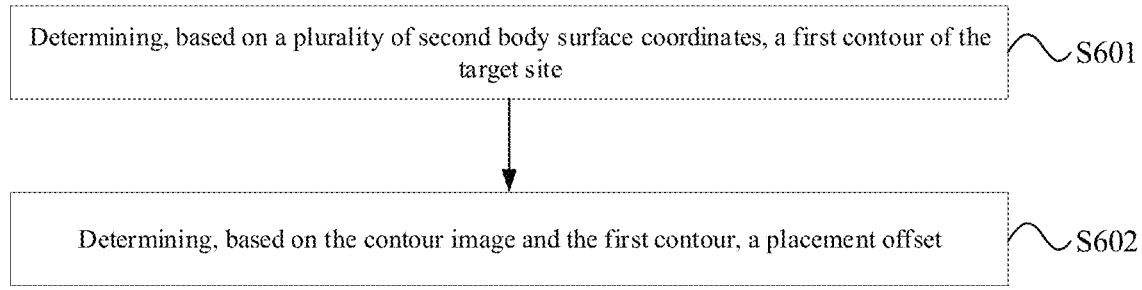
FIG. 6 is a flowchart of a method for determining a placement offset in a control method for positioning according to an embodiment of the present disclosure.

Based on the control method for positioning described in any of the above embodiments, the embodiments of the present disclosure further provide a possible implementation for determining a placement offset in the control method for positioning. FIG. 6 is a flowchart of a method for determining a placement offset in a control method for positioning according to an embodiment of the present disclosure. As shown in FIG. 6, determining, based on the plurality of second body surface coordinates and the contour image of the target site in the treatment plan, the placement offset of the target site under the isocentric coordinate system may include the following processes.

In S601, a first contour of the target site is determined based on the plurality of second body surface coordinates.

The plurality of second body surface coordinates are identified contour coordinates of the target site, such that the first contour of the target site, i.e. the actual contour of the target site in the case that the treatment couch is at the first placement position, may be determined based on the plurality of second body surface coordinates.

In S602, the placement offset is determined based on the contour image and the first contour.

Illustratively, a contour deviation of the target site may be determined by comparing the contour image with the first contour, and the placement offset may be calculated based on the contour deviation.

In the method provided by this embodiment, the placement offset can be determined by means of contour comparison based on the plurality of second body surface coordinates and the contour image, which can make the acquired placement offset more accurate and thus effectively ensure the accuracy of the subsequent positioning control.

Optionally, on the basis of any of the above methods, the method may further include: controlling the depth camera to acquire body surface information of the treatment object, so as to monitor the treatment object during treatment. The process may be performed upon completing the positioning. Completion of the positioning means that the placement offset of the target site upon movement meets the target offset requirement.

In the method provided by this embodiment, upon completing the positioning, the body surface information of the treatment object can be acquired, and the body surface information of the treatment object and corresponding acquisition time point may be recorded, such that the treatment monitor for the treatment object can be achieved without cooperating with an additional camera or transforming a matrix, which facilitates the subsequent treatment monitor.

An apparatus, device, storage medium, and the like for performing the control method for positioning provided in the present disclosure are described hereafter, and the specific implementing process and technical effects may be seen in the above embodiments and are not repeated herein.

Figure 7:
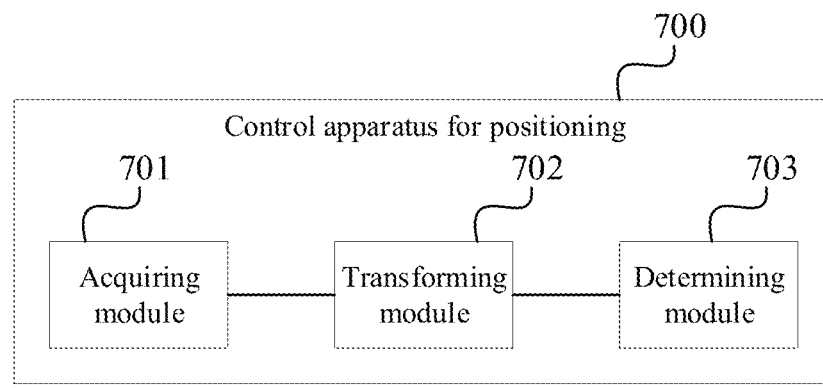
FIG. 7 is a schematic diagram of a control apparatus for positioning according to an embodiment of the present disclosure.

FIG. 7 is a schematic diagram of a control apparatus for positioning according to an embodiment of the present disclosure. The apparatus is applicable to any of the above radiotherapy systems. As shown in FIG. 7, the control apparatus for positioning 700 may include:

an acquiring module 701, configured to acquire a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;

a transforming module 702, configured to acquire a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and a determining module 703, configured to determine, based on the plurality of second body surface coordinates and a contour image of the target site in a treatment plan, a placement offset of the target site under the isocentric coordinate system, so as to control the treatment couch to move until the placement offset of the target site upon the movement meets a target offset requirement.

Optionally, the transforming module 702 is further configured to: prior to acquiring the plurality of second body surface coordinates of the target site under the isocentric coordinate system of the radiotherapy equipment by transforming the plurality of first body surface coordinates using the target transformation matrix corresponding to the first placement position, acquire the target transformation matrix by transforming, based on the first placement position and a second placement position of the treatment couch, a transformation matrix corresponding to the second placement position, wherein the second placement position is a placement position different from the first placement position.

Optionally, the transforming module 702 is further configured to: in the case that the treatment couch is a three-dimensional treatment couch, calculate a first amount of translation from the second placement position to the first placement position, and acquire the target transformation matrix by transforming, based on the first amount of translation, the transformation matrix corresponding to the second placement position.

Optionally, the transforming module 702 is further configured to: in the case that the treatment couch is a six-dimensional treatment couch, calculate an amount of rotation and a second amount of translation from the second placement position to the first placement position, and acquire the target transformation matrix by transforming, based on the amount of rotation and the second amount of translation, the transformation matrix corresponding to the second placement position.

Optionally, the second placement position is a calibrated placement position of the treatment couch, the control apparatus for positioning 700 further includes: a calibrating module, configured to acquire first coordinates of a target position in a depth image of a calibration phantom on the treatment couch, wherein the depth image is captured by the depth camera in response to the treatment couch being at the calibrated placement position, the first coordinates are coordinates under the camera coordinate system, and the target position is any position on the calibration phantom; determine, based on the first coordinates and a transformation relationship between the camera coordinate system and the treatment couch coordinate system, second coordinates of the target position under the treatment couch coordinate system; determine, based on the second coordinates and a transformation relationship between the treatment couch coordinate system and the isocentric coordinate system, third coordinates of the target position under the isocentric coordinate system; and calculate, based on the first coordinates and the third coordinates, a transformation matrix corresponding to the calibrated placement position.

Optionally, the determining module 703 is further configured to determine, based on the plurality of second body surface coordinates, a first contour of the target site; and determine, based on the contour image and the first contour, the placement offset.

Optionally, the acquiring module 701 is configured to control the depth camera to acquire body surface information of the treatment object, so as to monitor the treatment object during treatment.

The above apparatus is used to perform the control method for positioning provided in the preceding embodiments, and has a similar principle of implementation and technical effects with the control method for positioning provided in the preceding embodiments, which is not repeated herein.

These modules may be one or more integrated circuits configured to implement the above methods, e.g., one or more application specific integrated circuits (ASIC), one or more microprocessors (such as a digital signal processor, DSP), one or more field programmable gate arrays (FPGA), or the like. Further, in the case that one of the above modules is implemented in the form of a processing element dispatching a program code, the processing element may be a general-purpose processor, such as a central processing unit (CPU) or other processors that can call a program code. Further, these modules may be integrated together and implemented in a form of a system-on-a-chip (SOC).

Figure 8:
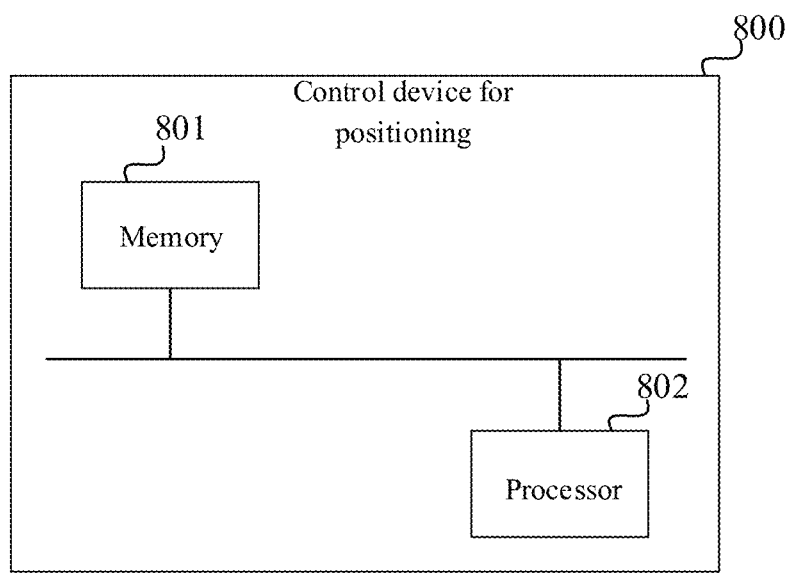
FIG. 8 is a schematic diagram of a control device for positioning according to an embodiment of the present disclosure.

FIG. 8 is a schematic diagram of a control device for positioning provided by an embodiment of the present disclosure, the control device for positioning may be integrated to a device or a chip of the device. The control device for positioning may be a device with a computational processing function, and may be communicatively connected to the above-mentioned depth camera.

The control device for positioning 800 is applicable to a radiotherapy system. The radiotherapy system includes radiotherapy equipment and a depth camera, the radiotherapy equipment including a radiation chamber and a treatment couch, and the depth camera is disposed at an end, distal from the radiation chamber, of the treatment couch. The control device for positioning 800 includes: a memory 801 and a processor 802. The memory 801 and the processor 802 are connected via a bus.

The memory 801 is configured to store a computer program, and the processor 802, when loading and running the program stored in the memory 801, is configured to perform any of the control methods for positioning described in the above method embodiments. The specific implementation and technical effects of the control device for positioning are similar to the control method for positioning, which are not repeated herein.

Optionally, the present disclosure also provides a program product, such as a computer-readable storage medium, which may be a non-transitory storage medium. The storage medium may include a computer program, wherein the computer program, when loaded and run by a processor of a device, causes the device to perform the method embodiments described above.

In the embodiments provided by the present disclosure, it should be understood that the disclosed apparatus and method may be implemented in other ways. For example, the apparatus embodiments described above are only illustrative. The division of the modules described above is only a logical functional division, and the modules may be divided in other ways in practice. For example, multiple units or components may be combined or integrated into another system, or some features may be ignored, or not implemented. In addition, the mutual coupling, directly coupling, or communication connection shown or discussed may be implemented by the indirect coupling or communication connection of some interfaces, devices, or units, which may be electrical, mechanical, or in other forms.

The units illustrated as separate components may be or not be physically separated, and the components displayed as units may be or not be physical units, i.e., the component may be located in one place or may be distributed at a plurality of network units. Some or all of these units may be selected depending on practical needs to achieve the purpose of the solution in the embodiments.

In addition, the functional units in embodiments of the present disclosure may be integrated into a processing unit, or each unit may physically exist separately, or two or more units may be integrated into one unit. The above-integrated units may be implemented in the form of hardware or in the form of hardware plus software functional units.

The above-integrated units, implemented in the form of software functional units, may be stored in a computer-readable storage medium. The above software functional unit stored in a storage medium includes a plurality of instructions, the plurality of instructions, when loaded and run by a computer device (which can be a personal computer, a server, or a network device, etc.) or a processor, cause the computer device or the processor to perform some of the processes of the method described in various embodiments of the present disclosure. The aforementioned storage medium includes: a USB flash disk, a mobile hard disk, a read-only memory (ROM), a random-access memory (RAM), a floppy disk or a compact disc, and other mediums that can store a program code.

The above embodiments are merely exemplary embodiments of the present disclosure and are not intended to limit the disclosure. Those skilled in the art may, within the spirit and scope of the present disclosure, may make various modifications or equivalent alterations to the disclosure, which are considered to be within the scope of the disclosure. Therefore, the scope of this disclosure is defined by the scope of the claims.

What is claimed is:

1. A control method for positioning, applicable to a radiotherapy system, the radiotherapy system comprising radiotherapy equipment and a depth camera, the radiotherapy equipment comprising a radiation chamber and a treatment couch, and the depth camera being disposed at an end, distal from the radiation chamber, of the treatment couch, the method comprising:
    acquiring a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;
    acquiring an isocentric coordinate matrix comprising a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and
    determining, based on the plurality of second body surface coordinates and a contour image of the target site in a treatment plan, a placement offset of the target site under the isocentric coordinate system, so as to control the treatment couch to move until the placement offset of the target site meets a target offset requirement.

2. The method according to claim 1, wherein prior to acquiring the plurality of second body surface coordinates of the target site by transforming the plurality of first body surface coordinates using the target transformation matrix corresponding to the first placement position, the method further comprises:
    acquiring the target transformation matrix by transforming, based on the first placement position and a second placement position of the treatment couch, a transformation matrix corresponding to the second placement position, wherein the second placement position is a placement position different from the first placement position.

3. The method according to claim 2, wherein the treatment couch is a three-dimensional treatment couch; and acquiring the target transformation matrix by transforming, based on the first placement position and the second placement position of the treatment couch, the transformation matrix corresponding to the second placement position comprises:
    calculating a first amount of translation from the second placement position to the first placement position; and
    acquiring the target transformation matrix by transforming, based on the first amount of translation, the transformation matrix corresponding to the second placement position.

4. The method according to claim 2, wherein the treatment couch is a six-dimensional treatment couch; and acquiring the target transformation matrix by transforming, based on the first placement position and the second placement position of the treatment couch, the transformation matrix corresponding to the second placement position comprises:
    calculating an amount of rotation and a second amount of translation from the second placement position to the first placement position; and
    acquiring the target transformation matrix by transforming, based on the amount of rotation and the second amount of translation, the transformation matrix corresponding to the second placement position.

5. The method according to claim 2, wherein the second placement position is a calibrated placement position of the treatment couch; and prior to acquiring the target transformation matrix by transforming, based on the first placement position and the second placement position of the treatment couch, the transformation matrix corresponding to the second placement position, the method further comprises:
    acquiring first coordinates of a target position in a depth image of a calibration phantom on the treatment couch, wherein the depth image is captured by the depth camera in response to the treatment couch being at the calibrated placement position, the first coordinates are coordinates under the camera coordinate system, and the target position is any position on the calibration phantom;
    determining, based on the first coordinates and a transformation relationship between the camera coordinate system and the treatment couch coordinate system, second coordinates of the target position under the treatment couch coordinate system;
    determining, based on the second coordinates and a transformation relationship between the treatment couch coordinate system and the isocentric coordinate system, third coordinates of the target position under the isocentric coordinate system; and
    calculating, based on the first coordinates and the third coordinates, a transformation matrix corresponding to the calibrated placement position.

6. The method according to claim 1, wherein determining, based on the plurality of second body surface coordinates and the contour image of the target site in the treatment plan, the placement offset of the target site under the isocentric coordinate system comprises:
    determining, based on the plurality of second body surface coordinates, a first contour of the target site; and
    determining, based on the contour image and the first contour, the placement offset.

7. The method according to claim 1, further comprising:
    controlling the depth camera to acquire body surface information of the treatment object, so as to monitor the treatment object during treatment.

8. A non-transitory computer-readable storage medium, storing a computer program, wherein the computer program, when loaded and run by a processor of a device, causes the device to perform the control method for positioning as defined in claim 1.

9. A control device for positioning, applicable to a radiotherapy system, the radiotherapy system comprising radiotherapy equipment and a depth camera, the radiotherapy equipment comprising a radiation chamber and a treatment couch, and the depth camera being disposed at an end, distal from the radiation chamber, of the treatment couch, the device comprising:
  a processor; and
  a memory configured to store a computer program executable by the processor;
  wherein the processor, when loading and running the computer program, is caused to:
    acquire an isocentric coordinate matrix comprising a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;
    acquire a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and
    determine, based on the plurality of second body surface coordinates and a contour image of the target site in a treatment plan, a placement offset of the target site under the isocentric coordinate system, so as to control the treatment couch to move until the placement offset of the target site meets a target offset requirement.

10. The device according to claim 9, wherein the processor, when loading and running the computer program, is further caused to:
  acquire the target transformation matrix by transforming, based on the first placement position and a second placement position of the treatment couch, a transformation matrix corresponding to the second placement position, wherein the second placement position is a placement position different from the first placement position.

11. The device according to claim 10, wherein the treatment couch is a three-dimensional treatment couch; and the processor, when loading and running the computer program, is further caused to:
  calculate a first amount of translation from the second placement position to the first placement position; and
  acquire the target transformation matrix by transforming, based on the first amount of translation, the transformation matrix corresponding to the second placement position.

12. The device according to claim 10, wherein the treatment couch is a six-dimensional treatment couch; and the processor, when loading and running the computer program, is further caused to:
  calculate an amount of rotation and a second amount of translation from the second placement position to the first placement position; and
  acquire the target transformation matrix by transforming, based on the amount of rotation and the second amount of translation, the transformation matrix corresponding to the second placement position.

13. The device according to claim 10, wherein the second placement position is a calibrated placement position of the treatment couch; and the processor, when loading and running the computer program, is further caused to:
  acquire first coordinates of a target position in a depth image of a calibration phantom on the treatment couch, wherein the depth image is captured by the depth camera in response to the treatment couch being at the calibrated placement position, the first coordinates are coordinates under the camera coordinate system, and the target position is any position on the calibration phantom;
  determine, based on the first coordinates and a transformation relationship between the camera coordinate system and the treatment couch coordinate system, second coordinates of the target position under the treatment couch coordinate system;
  determine, based on the second coordinates and a transformation relationship between the treatment couch coordinate system and the isocentric coordinate system, third coordinates of the target position under the isocentric coordinate system; and
  calculate, based on the first coordinates and the third coordinates, a transformation matrix corresponding to the calibrated placement position.

14. The device according to claim 9, wherein the processor, when loading and running the computer program, is further caused to:
  determine, based on the plurality of second body surface coordinates, a first contour of the target site; and
  determine, based on the contour image and the first contour, the placement offset.

15. The device according to claim 9, wherein the processor, when loading and running the computer program, is further caused to:
  control the depth camera to acquire body surface information of the treatment object, so as to monitor the treatment object during treatment.

16. A radiotherapy system, comprising: radiotherapy equipment, a depth camera, and one or more processors, the radiotherapy equipment comprising: a radiation chamber and a treatment couch;
  wherein the depth camera is disposed at an end, distal from the radiation chamber, of the treatment couch; and the one or more processors are connected to the depth camera and configured to perform a control method for positioning, wherein the control method for positioning comprises:
    acquiring a plurality of first body surface coordinates of a target site in a three-dimensional body surface image of a treatment object on the treatment couch, wherein the three-dimensional body surface image is captured by the depth camera in response to the treatment couch being at a first placement position, the first placement position being any position at which the treatment couch is placeable, and the plurality of first body surface coordinates are coordinates of a plurality of body surface positions in a region corresponding to the target site under a camera coordinate system of the depth camera;
    acquiring an isocentric coordinate matrix comprising a plurality of second body surface coordinates of the target site by transforming the plurality of first body surface coordinates using a target transformation matrix corresponding to the first placement position, wherein the plurality of second body surface coordinates are coordinates of the plurality of body surface positions in the target site under an isocentric coordinate system of the radiotherapy equipment, and the target transformation matrix is a transformation matrix between the camera coordinate system and the isocentric coordinate matrix; and determining, based on the plurality of second body surface coordinates and a contour image of the target site in a treatment plan, a placement offset of the target site under the isocentric coordinate system, so as to control the treatment couch to move until the placement offset of the target site upon meets a target offset requirement.

17. The system according to claim 16, wherein prior to acquiring the plurality of second body surface coordinates of the target site by transforming the plurality of first body surface coordinates using the target transformation matrix corresponding to the first placement position, the method further comprises:

acquiring the target transformation matrix by transforming, based on the first placement position and a second placement position of the treatment couch, a transformation matrix corresponding to the second placement position, wherein the second placement position is a placement position different from the first placement position.

18. The system according to claim 17, wherein the treatment couch is a three-dimensional treatment couch; and acquiring the target transformation matrix by transforming, based on the first placement position and the second placement position of the treatment couch, the transformation matrix corresponding to the second placement position comprises:

calculating a first amount of translation from the second placement position to the first placement position; and acquiring the target transformation matrix by transforming, based on the first amount of translation, the transformation matrix corresponding to the second placement position.

19. The system according to claim 17, wherein the treatment couch is a six-dimensional treatment couch; and acquiring the target transformation matrix by transforming, based on the first placement position and the second placement position of the treatment couch, the transformation matrix corresponding to the second placement position comprises:

calculating an amount of rotation and a second amount of translation from the second placement position to the first placement position; and acquiring the target transformation matrix by transforming, based on the amount of rotation and the second amount of translation, the transformation matrix corresponding to the second placement position.

20. The system according to claim 17, wherein the second placement position is a calibrated placement position of the treatment couch; and prior to acquiring the target transformation matrix by transforming, based on the first placement position and the second placement position of the treatment couch, the transformation matrix corresponding to the second placement position, the method further comprises:

acquiring first coordinates of a target position in a depth image of a calibration phantom on the treatment couch, wherein the depth image is captured by the depth camera in response to the treatment couch being at the calibrated placement position, the first coordinates are coordinates under the camera coordinate system, and the target position is any position on the calibration phantom;

determining, based on the first coordinates and a transformation relationship between the camera coordinate system and the treatment couch coordinate system, second coordinates of the target position under the treatment couch coordinate system;

determining, based on the second coordinates and a transformation relationship between the treatment couch coordinate system and the isocentric coordinate system, third coordinates of the target position under the isocentric coordinate system; and calculating, based on the first coordinates and the third coordinates, a transformation matrix corresponding to the calibrated placement position.

* * * * *